United States Patent
Buss (10) Patent No.: US 10,060,873 B2
(45) Date of Patent: Aug. 28, 2018

(54) TAPERED SOIL MOISTURE SENSOR ARRANGEMENT AND METHOD OF INSTALLATION

(71) Applicant: SENTEK PTY LTD., Stepney, S.A. (AU)

(72) Inventor: Peter Buss, Stepney (AU)

(73) Assignee: SENTEK PTY LTD., Stepney, S.A. (AU)

( * ) Notice: Subject to any disclaimer, the term of this patent is extended or adjusted under 35 U.S.C. 154(b) by 219 days.

(21) Appl. No.: 14/782,626

(22) PCT Filed: Apr. 10, 2014

(86) PCT No.: PCT/AU2014/000383
§ 371 (c)(1),
(2) Date: Oct. 6, 2015

(87) PCT Pub. No.: WO2014/165910
PCT Pub. Date: Oct. 16, 2014

(65) Prior Publication Data
US 2016/0061762 A1 Mar. 3, 2016

(30) Foreign Application Priority Data
Apr. 10, 2013 (AU) .............................. 2013901224

(51) Int. Cl.
*G01R 31/00* (2006.01)
*G01R 27/08* (2006.01)
(Continued)

(52) U.S. Cl.
CPC ......... *G01N 27/223* (2013.01); *G01N 33/246* (2013.01)

(58) Field of Classification Search
CPC ........................... G01N 27/223; G01N 33/246
(Continued)

(56) References Cited

U.S. PATENT DOCUMENTS

| 4,929,885 A | 5/1990 | Dishman |
| 5,260,666 A | 11/1993 | Dishman et al. |

(Continued)

FOREIGN PATENT DOCUMENTS

| AU | 760525 | 2/2000 |
| AU | 2002331464 B2 | 4/2003 |
| EP | 1 174 715 A2 | 1/2002 |

OTHER PUBLICATIONS

International Search Report issued in PCT/AU2014/000383, dated Jun. 2, 2014.

*Primary Examiner* — Farhana Hoque
(74) *Attorney, Agent, or Firm* — Birch, Stewart, Kolasch & Birch, LLP (57) ABSTRACT

A sensor housing having a body for housing a soil moisture sensor arrangement with sensors arranged within and along the length of the housing, the body is shaped so that there is a continuous taper from the head end having the larger outer diameter to the inserted end having the smaller outer diameter, and the volume of the opening created by an auger in the ground will provide a matching volume for the sensor housing of a predetermined volume such that the entire tapered outer surface of the sensor is adjacent the ground along the full length of the created opening. The sensors include at least a first capacitive element, and a second capacitive element that has a maximum outer diameter smaller than the maximum outer diameter of the first capacitive element.

21 Claims, 4 Drawing Sheets (51) Int. Cl.
*G01N 27/22* (2006.01)
*G01N 33/24* (2006.01)

(58) Field of Classification Search
USPC ................................. 324/323, 505, 694, 696
See application file for complete search history.

(56) References Cited

U.S. PATENT DOCUMENTS

| | | | |
|---|---|---|---|
| 5,341,673 A | 8/1994 | Burns et al. | |
| 5,418,466 A | 5/1995 | Watson et al. | |
| 7,042,234 B2 | 5/2006 | Buss | |
| 7,240,743 B2 | 7/2007 | Buss et al. | |
| 2003/0222662 A1* | 12/2003 | Geisel | G01N 27/045 324/664 |
| 2004/0238217 A1* | 12/2004 | Buss | G01N 1/08 175/20 |
| 2006/0139037 A1* | 6/2006 | Hughes | G01N 33/246 324/696 |
| 2006/0290360 A1* | 12/2006 | Lee | A01G 25/167 324/690 |

* cited by examiner

TAPERED SOIL MOISTURE SENSOR ARRANGEMENT AND METHOD OF INSTALLATION

The field of the invention is soil sensors and in particular the sensor elements and sensor element housings and methods and apparatus for the placement of the soil sensor housing in the soil.

BACKGROUND

The field of soil characteristics measurement and in particular soil moisture and salinity is described in various published patents and patent applications owned by the subject applicant, including U.S. Pat. No. 5,418,466; AU760525; AU2002331464; U.S. Pat. No. 7,042,234; and U.S. Pat. No. 7,240,743 all of which are incorporated by reference into this specification.

Although the arrangements disclosed in the abovementioned patents are workable there are always pressures to minimize costs and create easier, more time saving and more simply repeatable arrangements for installing sensors in the soil and measuring the moisture and salinity of the soil.

The invention disclosed herein provides one or more arrangements that are an improvement and/or alternative arrangement to those disclosed in the previously referred to patents and patent applications by the applicant.

BRIEF DESCRIPTION OF THE INVENTION

In one aspect of the invention there is a housing for a capacitive soil moisture sensor arrangement for use in a prepared opening in the soil, the housing having
  a) a body, the body adapted for housing a soil moisture sensor arrangement wherein sensors are arranged within and along the length of the housing, the body having a head end and an inserted end, the body shaped so that the maximum outer diameter of the inserted end is smaller than the maximum outer diameter of the head end of the body, and the body adapted to be inserted into the prepared opening such that the outer surface of the body is in conformance with the soil forming the prepared opening along the full length of the housing.

In a further aspect of the invention a method for installing a capacitive soil moisture sensor arrangement in soil having a housing as described in the previous paragraph, includes the steps of:
  a) preparing an opening in the soil having an inner wall converging to the region near the base of the opening; and
  b) inserting the housing into the prepared opening until the outer surface of the body of the housing is in contact with the soil sides of the prepared opening along the full length of the housing.

In a yet further aspect of the invention a capacitive soil moisture sensor arrangement for use in a prepared opening in soil includes:
  a) a housing with a head end and an inserted end having an inner surface and an outer surface, the inserted end for insertion into the prepared opening along the full length of the housing;
  b) a first capacitive sensor having with a maximum outer diameter located in the housing adjacent an inner surface of the housing;
  c) a second capacitive sensor located adjacent an inner surface of the housing and having a maximum outer diameter smaller than the maximum outer diameter of the first capacitive sensor, the second capacitive sensor being located closer to the inserted end of the housing than the first capacitive sensor,
wherein the housing, in use, is within the prepared opening and the outer surface of the housing is in contact with the sides of the prepared opening and the first and second capacitive sensors provide for the measurement of at least the moisture of the soil in which the sensor arrangement is inserted.

In a yet further aspect of the invention the capacitive sensor is substantially circular.

In yet a further aspect of the invention each of the capacitive sensors include at least two sensor elements of conductive material shaped, when in use, so as to have a central axis which is co-axial with other of the capacitive sensors.

In an embodiment of the invention a capacitive sensor includes at least two sensor elements of flexible conductive material.

In a yet further aspect of the invention a capacitive soil moisture sensor for use in a housing having a head end and an inserted end of smaller outer diameter than the head end to be inserted in a prepared opening in soil, including:
  a) a first capacitive element with a maximum outer diameter, and
  b) a second capacitive element having a maximum outer diameter smaller than the maximum outer diameter of the first capacitive element, the second capacitive element being spaced longitudinally along the housing from the first capacitive element and located closer to the inserted end than the first capacitive element,
wherein the first and second capacitive elements provide a capacitive sensor for the measurement of at least the moisture of the soil in which the housing is inserted.

In yet a further aspect of the invention a capacitive soil moisture sensor arrangement according to the previous paragraph, including:
  a) at least one capacitive sensor, including:
    a. a first capacitive element with a maximum outer diameter, and
    b. a second capacitive element having a maximum outer diameter smaller than the maximum outer diameter of the first capacitive element, the second capacitive element being spaced longitudinally along the housing from the first capacitive element and located closer to the inserted end than the first capacitive element, and
  b) a housing having a body, the body having a hollow space adapted for housing at least one soil moisture sensor, the body having a head end and an inserted end, the body shaped so that the maximum outer diameter of the inserted end is smaller than the maximum outer diameter of the head end of the body, wherein the body when inserted into the prepared opening is such that the outer surface of the body of the housing is in contact with the soil sides of the prepared opening along the full length of the housing.

In a further aspect of the invention the sensor elements are circular in shape.

In yet a further aspect the external shape of the body is in conformance with the outer shape of the sensor elements.

In an aspect of the invention the housing the body of the housing includes material that envelops multiple capacitive soil moisture sensor arrangements such that the sensors have a fixed location relative to the housing.

In a further aspect of the invention the body of the housing of a capacitive soil moisture sensor arrangement includes a flexible form into which two or more flexible capacitive soil moisture sensor arrangements are located and further includes a material which is located inside the flexible form which stiffens the flexible form such that the body can be inserted into a prepared opening in the soil.

In one aspect of the invention a depth datum is provided on an external portion of the body of housing to assist the insertion of the body into a prepared opening to a predetermined depth.

In another aspect of the invention there is a method of installation of a capacitive sail moisture sensor arrangement according to a previous paragraph the soil having an upper surface, the steps including:

a) preparing an opening in the soil having an inner wall formed when creating the opening wherein the opening has a maximum inner diameter at the soil surface larger than the maximum inner diameter near the bottom of the opening below the surface of the soil;

b) inserting the body of the housing and installed capacitive soil moisture sensor into the prepared opening and forcing the outer walls of the housing against the inner wall of the opening along the fully inserted length of the housing.

In a further aspect the prepared opening is sized to exceed the length of the housing.

In an aspect of the invention for use in the method of the invention described in at least the previous paragraph there is an auger used for preparing an opening suitable for the method of installation of the capacitive soil moisture sensor arrangement, the auger including, spiral flighting which has a larger outer circumference at the driven end of the body of the auger than the outer circumference at the inserted end of the body of the auger.

The greater the downward force on the sensor housing the greater the pressure and the greater likelihood there will be no gaps between the outer area of the sensor housing and the soil surface forming the opening.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The reference to any background or prior art in this specification is not, and should not be taken as, an acknowledgment or any form of suggestion that such background or prior art forms part of the common general knowledge.

Specific embodiments of the invention will now be described in some further detail with reference to and as illustrated in the accompanying figures. These embodiments are illustrative, and not meant to be restrictive of the scope of the invention. Suggestions and descriptions of other embodiments may be included within the scope of the invention but they may not be illustrated in the accompanying figures or alternatively features of the invention may be shown in the figures but not described in the specification.

DETAILED DESCRIPTION OF EMBODIMENTS OF THE INVENTION

The need for a quick and effective installation method for soil moisture sensor is one of the reasons for the creation of the method and means of this invention.

There are a number of aspects of the invention including in broad terms the following:

a housing for a capacitive soil moisture sensor arrangement;

an auger for forming an opening in soil suitable for the housing of a capacitive soil moisture sensor arrangement;

an auger stabilization base plate and screw pins to stabilize the auger during drilling to assist in the creation of a soil opening having a consistent side wall for accepting the tapered shape of the sensor housing along its full length;

an array of at least two a capacitive soil moisture sensors for use in the housing;

a capacitive soil moisture sensor arrangement installed in a housing;

a method for preparing an opening in the soil for the insertion of a housing for a capacitive soil moisture sensor arrangement; and a method of installation of a capacitive soil moisture sensor arrangement in a housing.

The workings of a soil moisture and optionally a salinity sensor are adequately described in the reference patent applications in the name of the applicant as previously referred to, so that information will not be repeated herein, suffice to emphasize that there is a fundamental need for the sensor housing and hence the capacitive sensors within the housing to have in use, a conformance with the surrounding soil as can be achieved as a result of the design of the housing and sensor and the installation method used, for all those reasons espoused in the referenced patents.

The sensor (preferably a capacitive sensor) of this invention may be used as part of a measuring network including sensor circuitry which also reads multiple sensors which can temporarily store and/or transmit sensor data to an appropriate computer facility, data logger or hand held device.

Additionally the raw data of the sensor may be processed using integrative models, that produce easily comprehensible trends and graphs, which aid the crop manager in making decisions related to management of irrigations and horticultural practices affecting crop production.

The processes of collecting, storing, transmitting, calibrating, processing, and displaying data into critical values, pictures, graphs, trends, thresholds, tables, forecasts and recommendations to obtain an easy to use decision making tool for the purpose of irrigation scheduling are not described in detail in this specification.

Figure 1:
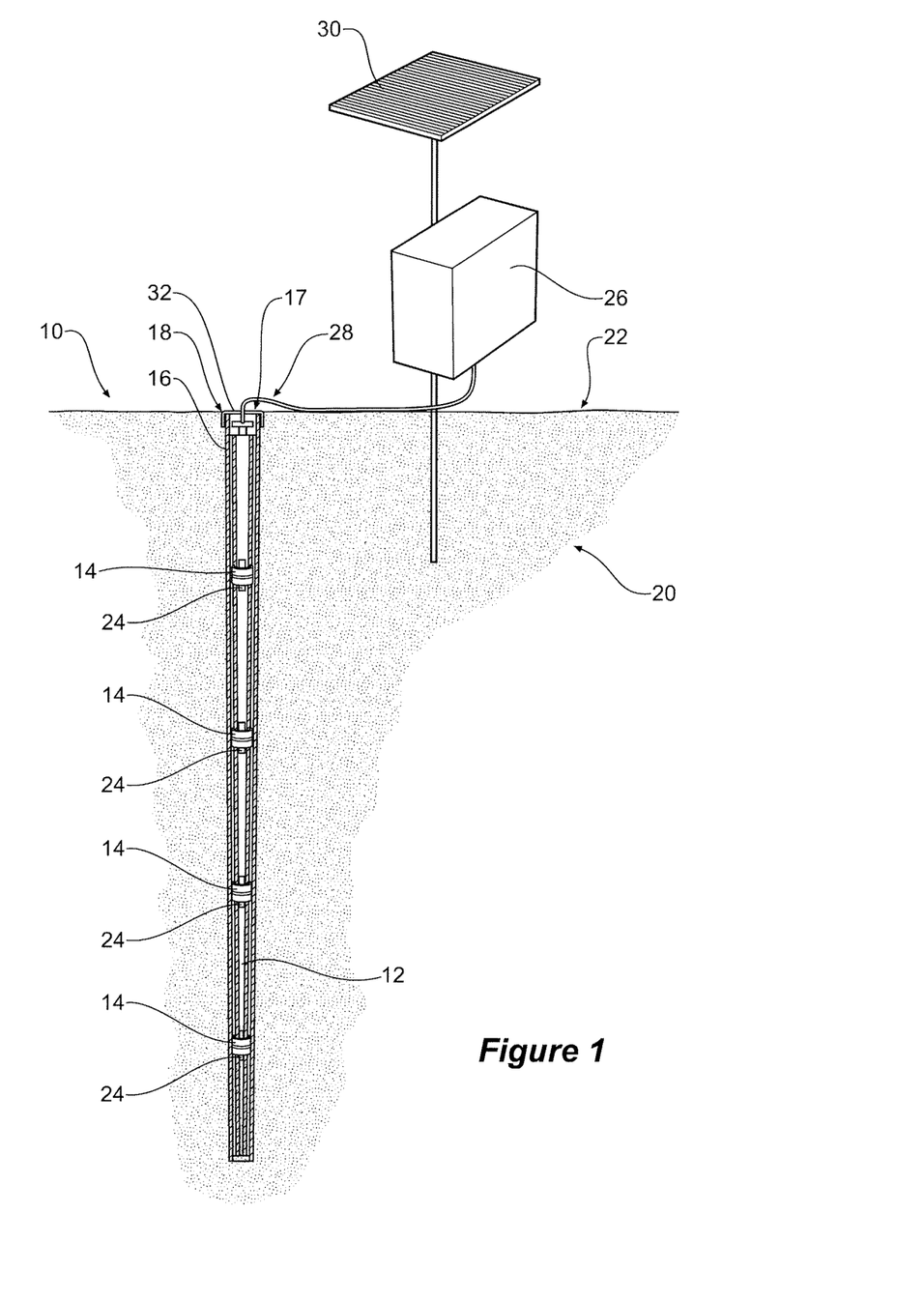
FIG. 1 depicts a cut-away view of an embodiment of a soil moisture sensor arrangement installed in the soil.

FIG. 1 depicts an embodiment of a capacitive soil moisture sensor arrangement 10, in situ, comprising a support frame 12 for accommodating an array of capacitive sensors 14 located within a housing 16 which has an open top end and a closed bottom end. The open top end can be sealed with a cap 17, although in an embodiment the sensor housing is sealed against environmental ingress, such as moisture in gaseous or liquid form by filling the housing with a towable material which hardens and thus does not have a separate top and all communication of data is wired or wireless. The housing is lowered into a prepared opening 18 in the soil 20, which has a surface 22 until the whole of the length of the housing is within the soil. The internal diameter of the housing 16 is shaped so as to allow the placement of the capacitive sensors 14 in proximity of the inner wall of the housing and therefore adjacent to and close to the surrounding soil.

It has also been found to be preferable that the prepared opening in the ground is shaped so that the housing is a close fit to the surrounding soil so that the sensors that are placed therein are also close to the soil to be monitored. The presence of air gaps near the outer wall of the housing 16 have been found to adversely affect the accuracy and repeatability as well as the absolute value of the measurements taken from the sensors in the vicinity of those gaps. Additionally the presence of air gaps can upon the occurrence of a rain or irrigation event, allow a flow of water and possibly also the creation of pools of water that lie adjacent, during and after the rain or irrigation event, the sensor housing and hence the sensors, and the presence of that water adversely affects the accuracy and relevance of any measurements taken before, during, and after the rain event particularly soil moisture and salinity measurements.

Any appreciable air gap may artificially reduce the density of the soil surrounding the access tube and may fill at times with water. In the first instance the air gap may distort the sphere of influence of the sensor and reduce the values of any measurements, in particular moisture and salinity measured and in the second instance water may distort and reduce the sphere of influence and of course may adversely affect the measured values Capacitive sensors 14 are shown spaced longitudinally apart along a support frame 12, which for the purpose of this embodiment are respectively at 10, 20, 30, . . . centimeters below the surface of the soil (not shown in scale in FIG. 1 but illustrated pictorially). During the course of the monitoring procedure the capacitive sensors 14 remain in those positions. A datum indicator can be provided, in one form being a visible (embossed or raised shape) line around the outer of the body of the housing of the sensor arrangement positioned at a predetermined location along the length of the body. In another form the top of the housing can be the level to which the housing is inserted into the prepared opening. A datum indicator allows the reasonably accurate location of the capacitive sensors at the depths in the soil, indicated above, when the housing is inserted into the prepared opening, when the datum line is coincident with the soil surface. It can be noted that the soil surface is a known level readily determined in the field since it is the surface of the soil through which the crop will emerge and downwards of which the crop root system is located. The soil moisture, one embodiment, being measured by the sensor arrangement is intimately related with the development of the root system of the crop.

An electronic circuit 24 is shown adjacent the capacitive sensors 14 and is used to transduce changes in the characteristics of adjacent capacitive sensors the signals of which represent, in one embodiment, the moisture and optionally the salinity in the surrounding soil 20 at predetermined time intervals and thus can be used to assess changes over time.

Preferably the electronic circuit 24 is located adjacent its respective sensor upon the support frame 12, although m one embodiment the frame is in the form of a printed circuit board which is electrically attached to electrically conductive regions on a flexible substrate, which forms the capacitive elements of a capacitive sensor 14. The adjacency minimizes spurious signals being picked up on any interconnecting cables between the sensor and the circuit. Each electronic circuit includes the other required parts of a tuned circuit with which the capacitive elements interacts and that circuit is also adapted to provide a signal representative of, in one embodiment, the moisture and optionally the salinity and temperature of the surrounding soil that is then communicated to a data collection device 26 via multi-stranded cable 28 or a printed circuit or another embodiment wirelessly from the sensor arrangement and external of the housing. In the embodiment depicted in FIG. 1, the location of a data collection device is adjacent to the in situ sensor apparatus 10 so that the effect of signal loss and spurious signal interference is minimized on the cable which is usable in such a configuration. However, it is not an ideal configuration since the physical space used takes away from the arable land available, it interrupts the tilling and tending of the crop in the immediate vicinity and adds another set of equipment that needs to be visited and maintained, hence in an embodiment not explicitly shown, the communication of data from the sensor array is via wireless means. In an embodiment the collected data is communicated external of the sensor housing using a wireless communication arrangement. In one preferred arrangement the data is communicated using Bluetooth™ to a mobile device, such as for example a Smart Phone on which an application is available to receive and process sensor data. The Bluetooth™ arrangement would likely be but not limited to being provided within the sensor housing.

Power for the sensor arrangement and the data collection device 26 is provided from batteries (not shown) located adjacent the data logger, which are in turn charged by numerous power source options, solar-electric convertor (solar panels) 30 and in other embodiment and electromagnetic contactless charger placed into proximity of the housing.

A cap 32 is optionally located over the upper opening of the housing 16 to assist the prevention of the ingress of rain, dirt and insects and thus protect the sensor apparatus from environmental damage.

The above configuration is but one example of a suitable capacitive soil moisture sensor arrangement.

Another configuration not depicted in the figures, includes a fully environmentally encapsulated sensor arrangement, wherein the sensors are positioned within a fully scaled body form and the data output uses an electrical cable or wireless signal, through which signaling representative of at least the collected soil moisture and salinity data, but which may also include, temperature, testing routine data, timing data, etc. while there is also a self-contained power supply within the sealed body form and if desired contacts which allow for wireless external charging of the power supply, such as for example a battery.

There are many forms in which a capacitive sensor can be created and installed into the body of the form described herein. In one form the sensors which make up an array of capacitive sensors is located within the housing fixed there relative to the housing when the housing is filled by a liquid which solidifies to not only fix the sensors into place but also provide rigidity to the housing.

Figure 2:
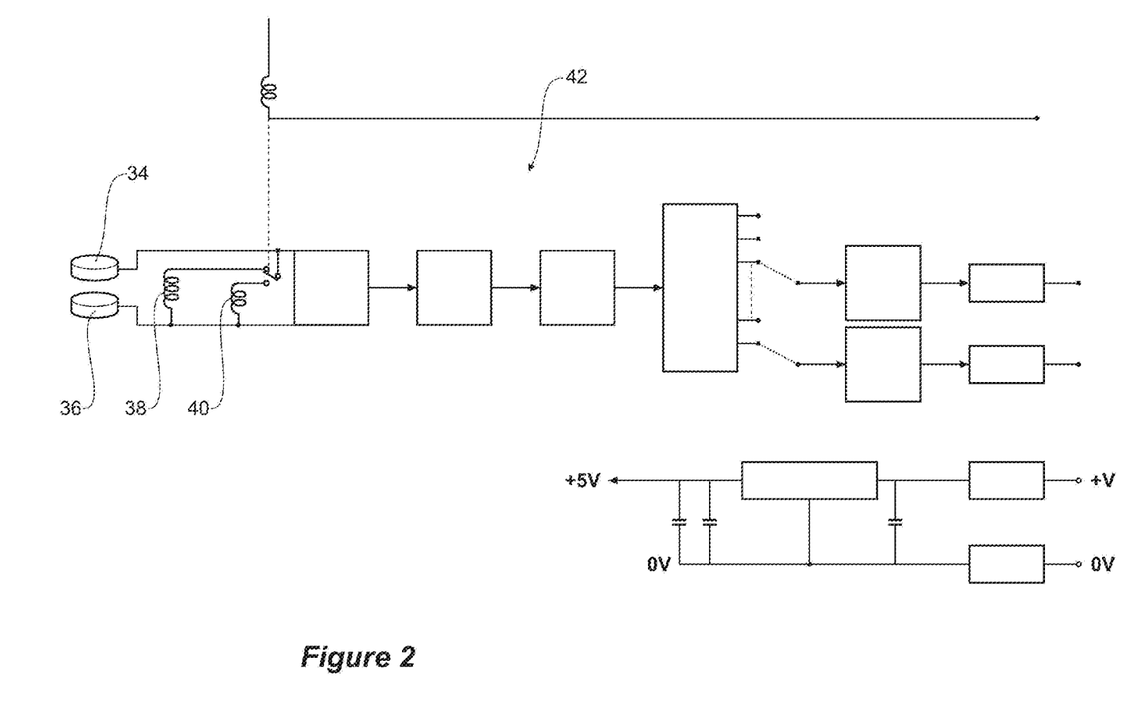
FIG. 2 depicts a schematic representation of part of a circuit of a soil moisture sensor arrangement.

FIG. 2 depicts a functional block diagram of the soil moisture and salinity sensor and its associated electronic sensor characteristic detection and transmission circuits. Capacitive (34, 36) and inductive (38, 40) elements in various combinations form an L-C tuning network for oscillator circuit 42.

In this embodiment the sensor comprises capacitive elements in the form of upper 34 and lower 36 conductive rings which, in use, are disposed in longitudinally spaced relationship to each other to maintain a constant gap (which may be air but which can be calibrated to work with the existence of any intervening material) and located in the soil (or other medium to be measured) in a manner depicted in FIG. 1.

In an embodiment the rings are formed on a flexible substrate, which is configured to form rings of electrically conductive material, where the rings have different diameters or at least pairs of rings are of very similar diameter while pairs of rings forming a capacitive sensor are longitudinally spaced apart along the length of the housing having larger or smaller diameter depending on whether they are closer to the head end or inserted end of the housing.

The remainder of the circuit depicted in FIG. 2 is described in detail in U.S. Pat. No. 5,418,466 and will not be described herein. This circuit is used by way of example only and is not the subject of this invention.

Figure 3:
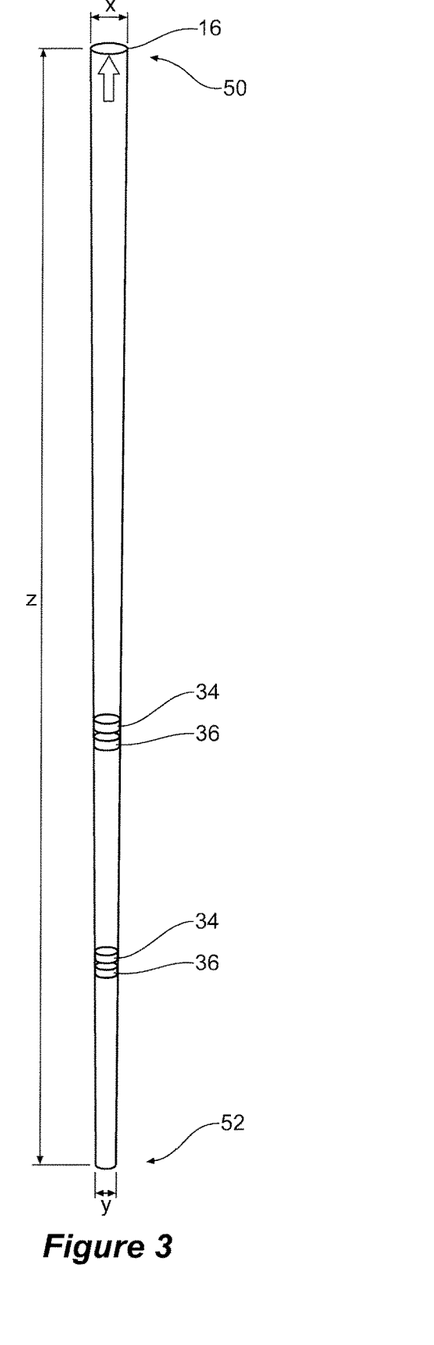
FIG. 3 depicts a cut-away side view of two soil moisture sensors located in a housing.

FIG. 3 depicts an embodiment of the housing for a soil moisture sensor arrangement for use in a prepared opening in the soil, as depicted in FIG. 1.

The housing has a body adapted for housing a soil moisture sensor arrangement. The adaptation in one embodiment is such that an array of capacitive soil moisture sensors pre-mounted to a framework or printed circuit board will fit by having the body adapted to have a tapered inner wall shape that is shaped to accommodate the particular sensor array and may in one embodiment be adapted in shape in the vicinity of each capacitive sensor.

A capacitive sensor includes two capacitive elements and first and a second which are spaced longitudinally along the housing, the first capacitive element being spaced from the second capacitive element and the second being located closer to the inserted end than the first.

Multiple of these capacitive sensors can be arrayed along the length of the inside of the body of the housing, spaced longitudinally along the housing from head end to the inserted end each individually associated with a tuned circuit.

In an embodiment, the body has a flexible form into which a flexible form of capacitive sensor is located. The flexible capacitive sensor is formed by conductive plastic material which can be folded or at least deformed to be placed into the housing via an open top region or in another embodiment passed through an aperture in the flexible form of the body and have some resilience and tendency to conform to the preferably rounded inner wall of the flexible body and when located appropriately along the internal length of the body ready to be connected as required with other capacitive sensors and an external communication arrangement, to permit the data collected or the data locally processed.

A particular form of a capacitive sensor is described in Australian Provisional patent application 20014901327 filed 10 Apr. 2014 in the name of the present applicant the content of which is incorporated in full by reference into this specification. In an exemplary form, an array of capacitive sensors is formed on a flexible carrier; such as a sheet of plastic or polyimide, and the sensor can be wrapped into a substantially circular cross-sectional that is also tapered so that one end has a larger diameter that the other end. In an embodiment the sheet on which the capacitive sensor is created is formed with at least one pair of opposite sides having non-parallel sides which can be housed within a housing of the form described herein because the shape of the sheet folds and fixes into a tapered form. A single sheet has the elements to provide for three sensors and an array of such sensors is created by aligning the sheets to have co-incident longitudinal axes while also providing for the increasing diameter of taper along the length of the housing.

The mention of circular cross-section is exemplary only as the shape of the sensor need not be circular to perform its sensing task, although it is preferable that the sensor conform to the inner wall shape of the housing and that the outer wall shape is the same as the inner wall shape in cross-section so that the sensor is located so as to be in proximity to the soil in which the housing is inserted.

In yet another form, the flexible sensor or sensor carrier is fed inside a housing and positioned adjacent the inner wall of the housing, which is substantially circular in cross-section. The inside of the housing can be filled with material so as to fix the sensors and other apparatus in location within the housing. The filling material will be electrically non-conducting and may contribute to the stiffening of the housing, for example, flowable polyurethane that solidifies to provide a high compressive strength and rigidity.

The capacitive sensors can be arranged to be adjacent but spaced from the inner wall of the body of the housing such that the flowable material fully surrounds the sensor elements and arrangement of sensors and eventually solidifies about them to then fix their physical location with respect to the housing and also maintain their electromagnetic characteristics so that those characteristics are the same even after being transported, stored and installed. This is an important feature since the repeatability and longevity of the sensor array is greatly enhanced.

The inside of the housing will thus contain appropriately positioned arrays of sensors, which are at the same time arranged to be connected with a respective capacitive sensor circuit and those circuits are arranged to communicate their respective signals external of the housing (most preferably by wireless communications).

Figure 4:
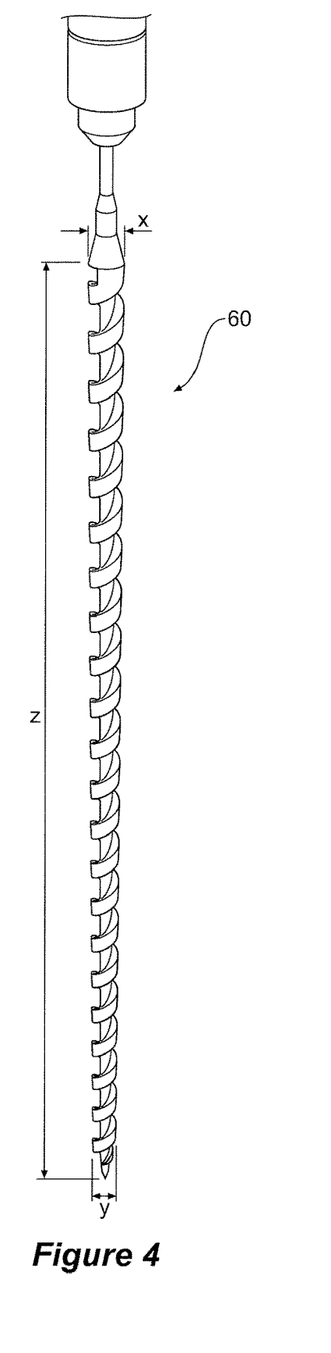
FIG. 4 depicts a side view of an embodiment of an auger suitable for the creation of a suitable opening in the ground to accept the full length of the housing.

The body of the housing 16 having a head end 50 and an inserted end 52, the body shaped so that the maximum outer diameter of the inserted end is smaller than the maximum outer diameter of the head end of the body, in this embodiment x=30 mm and y=24 mm and the length z of the housing is 1200 mm while in FIG. 4 the length z of the auger is 190 mm longer than the z of the housing in FIG. 3. The outer shape of the body is shaped for ease of insertion of the inserted end into a prepared opening 18 in the soil (FIG. 1) in that there is a generally a cone shape, in the case where the housing is generally circular in cross-section, as is pictorially depicted in FIG. 3.

However, if the housing were oblate or even square or rectangular in cross-section it would still be possible for the housing to accommodate an array of suitably shaped capacitive soil moisture sensor arrangements on a suitably shaped framework. It may also be that the body of the housing has these shapes along predetermined portions of its length. Furthermore the internal wall/s of the housing would also be adapted to allow the capacitive elements to lie adjacent the inner wall when the framework is inserted into the housing, and further the external shape of the body of the housing is in conformance with the outer shape of the capacitive sensor, whatever its shape, so as to permit the capacitive elements of the sensor to lie close to the inner walk of the prepared opening in the soil and for conformance of the outer shape of the body with the soil forming the prepared opening so that the sensors are in proximity to the soil in which the housing is inserted. Proximity can be a matter of adjacency with no spacing, or within an electromagnetically acceptable spacing, taking the thickness of the housing and any other gap into consideration. One embodiment of such an arrangement may include a sheet of flexible material on which is located electrically conductive areas forming part of a tuned circuit wherein the sheet material has tabs deformable to project outward of the sheet toward the inner wall of the sensor housing and positioned about the sheet when formed to fit within the housing so as to centralize the sheet within the inner walls of the housing.

In an embodiment where the housing has a circular cross-section which tapers from the head end 50 down to the inserted end 52, the shape of the prepared opening in the soil needs to be complementary, in that the opening is also of a circular cross-section which tapers from the soil surface down to the lowest region of the opening. To create such an opening it is proposed to use an auger with particular characteristics not normally found in augers.

An auger 60, referring to FIG. 4, suitable for creating an opening with the characteristics described above, has in one embodiment a spiral fighting which has a larger outer circumference X at the driven end of the body of the auger than the outer circumference Y at the inserted end of the body of the auger of a 190 mm greater length of Z as is illustrated in FIG. 4. The dimensions of the auger can be determined by knowing that the housing to be inserted into the prepared opening in the soil will be of a predetermined x, y and z dimension. In the case of a housing of the following dimension x=30, y=24 and z=1200 mm the auger dimension can be the same or slightly smaller, such as for example, x=29 mm, y=23 mm at least at the 1200 mm depth z.

Most efficiently the driver of the rotation of the auger is by an electric drill of about 150 watts power capable of rotating the auger in a variety of soil types at least at 550 revolutions per minute. Those requirements are for guidance only and the user of the equipment will best judge the power requirements and efficiently conduct the drilling step of the process ensuring safety at the same time.

A suitable auger dimension may depend on soil type and the complimentary housing shape and material it is made of. A particular form of an auger and method of manufacture is described in Australian Provisional patent application 20014901321 filed 10 Apr. 2014 in the name of the present applicant the content of which is incorporated in full by reference into this specification.

It may be necessary to provide an arrangement (not shown) to stabilize the auger while it is being used to create the opening in the ground, wherein the arrangement directs the applied directly downward force to auger while it is rotating and minimizes any sideways forces during the excavation of soil from the ground. The arrangement may include a frame having a cylindrically shaped collar through which the auger is placed that provides a guide to the direction of the auger during the time it is operating, the frame being anchored to the ground is suitable manner.

The method of installation of a capacitive soil moisture sensor arrangement according to any previous description when installed in a housing for use in a prepared opening in soil includes the steps of preparing an opening in the soil, where the opening has an inner wall formed when creating the opening such that the opening has a maximum inner diameter at the soil surface larger than the maximum inner diameter near the bottom of the opening below the surface of the soil so that substantially the full length of the housing is within the soil and the outer surface of the body of the housing is in contact with the inside wall of the prepared opening in the soil along substantially along the full length of the housing, indicating that the housing has been fully inserted into the prepared opening. The importance of fully inserting the housing come about because having the soil match the outside shape of the housing minimizes the potential for gaps and that minimizes or eliminates the air and water distortion to soil moisture and salinity measurements that are being recorded by the sensor array within the housing. The step of creating an aperture is best achieved using an auger of the description provided above but there might be other means and methods for achieving the form of an opening described.

In a preferred arrangement for preparing an opening it is sized to exceed the length of the housing so that the created extra hole space can accept soil that falls away from the auger during auger soil extraction without compromising the intended depth of the opening for full insertion of the sensor housing, such that the outer walls of the housing fit against the inner wall of the opening along the fully inserted length of the housing and where a depth of insertion datum line or indicator is used on the outer visible surface of the housing or the top of the housing is the datum then the full length of the encapsulated sensor within the housing lies within the prepared opening.

The body of the housing is adapted to be inserted into the prepared opening such that the outer surface of the body is in conformance with the soil forming the prepared opening along the full length of the housing.

The process of preparing an opening in the soil having an inner wall converging to the region near the base of the opening suitable for inserting the soil moisture sensor housing is achieved using an auger of the type described herein. The shape of the opening is determined by the outer shape of the auger but is arranged so that the opening is formed such that the outer surface of the body of the housing will be in contact with the soil sides of the prepared opening along the full length of the housing. The opening will generally have an inner will converging to the region near the base of the opening.

It will be apparent to those used to preparing an opening for the soil moisture sensor arrangements disclosed in the referenced patents in this specification that the preparation time and installation time is for those types of sensor housings in the order of 30 to 60 minutes as compared with less than 10 minutes for the sensor arrangement and housing disclosed in this specification, thus providing a great advantage to the installer typically the crop grower) over the installation using prior arrangements, installation equipment and methods of installation.

The next step of installation is inserting the body of the housing (as described above by way of numerous embodiments) and the sensor or sensor array located within the housing into the prepared opening and by forcing the outer walls of the housing are forced against the inner wall of the opening along the inserted length of the housing or most preferably along the full length of the housing. This step is possible when using a housing, which is of the form described above, wherein the head end of the housing has a maximum outer diameter larger than the maximum outer diameter of the inserted end of the housing. In particular, it is preferable for the outer wall/s of the housing to conform to the inner wall/s of the prepared opening. A maximum outer diameter measurement criteria would equally apply if the cross-sectional shape of the housing was other than circular, so by way of example only, if the housing had an oblate cross-sectional shape along the longitudinal length of the housing, the maximum diameter can still be determined at both the head end and inserted end as well as at the surface and bottom of the prepared opening.

Figure 5:
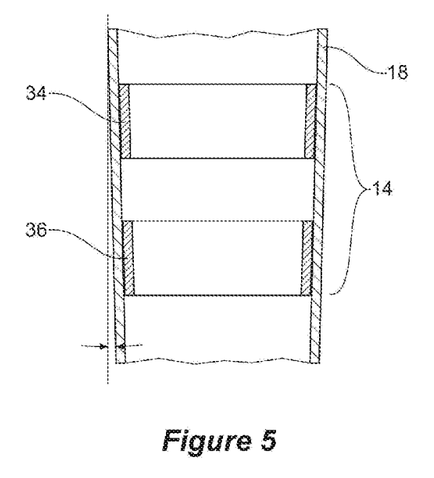
FIG. 5 depicts a close-up exploded side perspective view of two soil moisture sensor elements in a housing.

An embodiment of a capacitive soil moisture sensor element 14 for use within the housing is depicted in FIG. 5. The housing 18 is depicted having an exaggerated convergence of the inner wall of the housing, for an embodiment where the housing 18 has a circular cross-section and sensor elements 34 and 36 are formed from circular conductive rings. The exaggerated convergence of the housing wall possibly also exaggerates the divergence of the wall outwards from the top of each of the rings, but in practice the difference is very small and the outer wall of each ring will readily conform to the inner wall of the housing. Conform does not necessarily mean touch but may include the form of the sensor element being evenly spaced from the inner wall.

Furthermore the exaggerated convergence is used to illustrate that the maximum outer diameter of each ring is slightly different, with the illustration showing that the upper ring in the figure (closer to the head end of the housing) has a slightly larger diameter than the lower ring in the figure (closer to the inserted end of the housing), whereas in practice the rings may have very closely matched diameters but still be different. The outer diameter of a ring is easily determined but the outer diameter of a sensor with a shape different from a ring can also be determined by measuring between the widest part of the sensor shape as seen from a side view of the shape when in use such that the nominal center of the shape is co-axial with the longitudinal axis of the longitudinal housing. The outer diameter of a capacitive sensor is the maximum of the diameters of the larger (if there is a difference) of the two capacitive elements that form the capacitive sensor.

FIG. 3 shows a partial perspective view of ring shaped capacitive sensors, arrayed in pairs along the length of the housing. The longitudinal axis of the housing is not shown but is the nominal central axis to the generally circular cross-sectional housing which as described earlier tapers in maximum outer diameter from x distance at the head end 50 to y distance at the inserted end 52. The longitudinal axis of the sensors will typically be co-axial with the minimal central axis of the housing when they are installed and eventually fixed in relation to the housing.

As for the electromagnetic characteristics of the shaped sensors, rings in the depicted embodiment, they will most likely be substantially the same and work together so as to provide a capacitive soil moisture sensor 34, 36 regardless of any minor difference in diameter when part of a tuned circuit.

Much the same is also the case if the capacitive soil moisture sensor has other than a circular cross-sectional shape of metallic ring form, such as oblate or even rectangular or square, since in use in a tuned circuit those elements will still act to detect changes in the surrounding sphere of influence of the sensor and assist the determination of absolute values of moisture/complex dielectric constant and salinity in the adjacent soil. As mentioned previously each capacitive sensor element is made of conductive material which can be flexible but located so as to conform with the inner wall shape of the housing, or located within a walled structure that with further processing becomes a sensor housing able to be inserted into a prepared opening in the soil.

Not shown in FIG. 5 is the additional capacitive soil moisture sensor element 14 thus forming an array of at least two capacitive soil moisture sensor elements for use in a tuned circuit and located within the housing as is pictorially shown in FIGS. 1 and 3. In practical arrangements there will be pairs of capacitive soil moisture sensor elements 14 longitudinally spaced about 10 centimeters apart, along the full depth/length or part of the depth/length of the housing, or there may be, depending on the crop in the surrounding soil, clusters of capacitive soil moisture sensor elements 14 located along the depth of tire housing. As disclosed in the referenced patents in the name of the applicant the positioning of the capacitive soil moisture sensor elements can be used to obtain valuable information about the crop and its water uptake over time.

Figure 6:
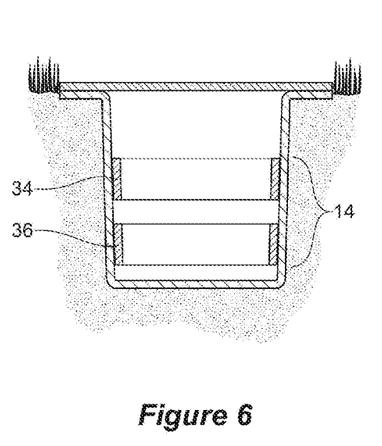
FIG. 6 depicts a cut-away side view of another embodiment of a soil moisture sensor elements installed in the soil.

FIG. 6 depicts a cut-away view of another embodiment of a soil moisture sensor arrangement installed in the soil, which in this case is a turf environment where the depth at which measurement needs to take place is shallow soil, as compared to crop environments. In the views provided in FIGS. 6 and 7 this embodiment of the housing still has the characteristics described above but the depth of the housing is much less that indicated is the case for the earlier described embodiment, being about 250 mm. In this embodiment the sensor elements and the housing have circular cross-sectional shape in the horizontal plane, when in use.

Figure 7:
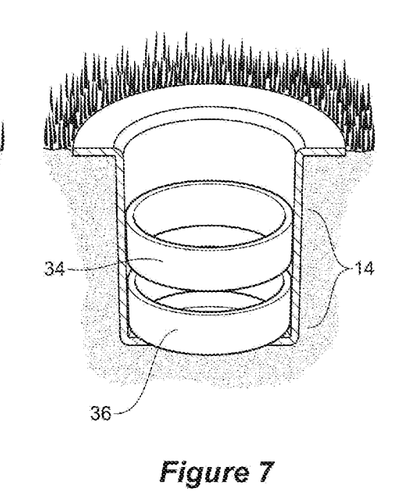
FIG. 7 depicts a cut-away perspective side view of the embodiment of a soil moisture sensor elements depicted in FIG. 6.

FIG. 7 depicts a cut-away perspective view of the embodiment of a soil moisture sensor arrangement depicted in FIG. 6. As is the case in both FIGS. 6 and 7 the individual sensor elements 34 and 36 are shown longitudinally spaced apart to create the capacitive component of the soil moisture determination circuit depicted, as one embodiment of such a circuit, in FIG. 2. The figures are illustrative and there may be more than one sensor located in the housing and the dimensions of the sensors are exaggerated in the figures to ensure clarity.

To create the opening in the soil (turf base material) a post hole digger having a slightly convergent sidewall is used. The great advantage of this arrangement is that during insertion of the housing into the prepared opening, the convergent inner wall of the opening tends to be readily conformed to by the convergent outer wall of the housing to create little or no gaps between the sensor elements and the surrounding soil.

In relation to all of the embodiments disclosed in this specification the creation of the opening in the soil is appreciably simpler than prior methods and the shape of the housing conforms with the prepared opening to bring the capacitive soil moisture sensor elements close to the surrounding soil with the added benefit of minimization or elimination of air gaps and consequent water pooling between the housing and the surrounding soil.

A reason to use a tapered sensor housing in a prepared tapered opening in the ground is the realization that the elimination of a gap is assured because the downward motion of the sensor into a complementary shaped opening ensure that the outer surface of the sensor housing will apply an pressure over the total outer area of the full inserted length of the sensor housing against the soil surface forming the opening. The greater the downward force on the sensor housing the greater the pressure and the greater likelihood that there will be no gaps between the outer surface area of the sensor housing and the soil surface forming the opening.

Thus there is a reason to provide a sensor array that also conforms in shape and arrangement the inside wall of the housing which also includes smaller diameter rings for each pair of capacitive elements as they are located further down (with respect to the head end of the sensor housing) the elongate sensor housing.

It will be appreciated by those skilled in the art that the invention is not restricted in its use to the particular application described. Neither is the present invention restricted in its preferred embodiment with regard to the particular elements and/or features described or depicted herein. It will be appreciated that various modifications can be made without departing from the principles of the invention. Therefore, the invention should be understood to include all such modifications within its scope.

The invention claimed is:

1. A soil moisture sensor arrangement for use in a prepared opening in soil including:
   a housing including an elongate body with a head end, an inserted end, and an outer surface being continuously tapered from the head end to the inserted end to form a hollow space therein, and
   at least one soil moisture sensor located within the hollow space of the housing,
   wherein, in use, the housing is located within the prepared opening and the outer surface of the housing is in conformance with the surface of the prepared opening along substantially the full length of the housing and each soil moisture sensor provides for the measurement of at least the moisture of the soil in which the sensor arrangement is inserted, and
   wherein a volume of the opening created by an auger in the ground will provide a matching volume for the housing of a predetermined volume such that the entire tapered outer surface of the sensor housing is adjacent the ground along the full length of the created opening.

2. The soil moisture sensor arrangement according to claim 1, wherein there are at least two soil moisture sensors being capacitive sensors, each capacitive sensor including at least two sensor elements of conductive material shaped, when in use, to have a common central axis which is co-axial with other of the capacitive sensors located within the housing, and
   wherein for each of the capacitive sensors, there is a first capacitive element of the sensor having a maximum outer diameter, and a second capacitive element of the sensor having a maximum outer diameter smaller than the maximum outer diameter of the first capacitive element.

3. The soil moisture sensor arrangement according to claim 2, wherein each capacitive sensor is substantially circular.

4. The soil moisture sensor arrangement according to claim 3, wherein each capacitive sensor includes elements of flexible conductive material.

5. The soil moisture sensor arrangement according to claim 3, wherein the external shape of the housing is in conformance with the outer shape of the sensor elements.

6. The soil moisture sensor arrangement according to claim 3, wherein within the hollow space of the body of the housing includes a flowable and solidified material that envelops all of the at least two capacitive soil moisture sensor elements such that the capacitive soil moisture sensor elements have a fixed location relative to the housing.

7. The soil moisture sensor arrangement according to claim 3, wherein the body of the housing includes a flexible form into which two or more soil moisture sensor elements are located and further includes a material which is located inside the flexible form which stiffens the flexible form such that the body can be inserted into a prepared opening in the soil.

8. The soil moisture sensor arrangement according to claim 2, wherein each capacitive sensor includes elements of flexible conductive material.

9. The soil moisture sensor arrangement according to claim 8, wherein the external shape of the housing is in conformance with the outer shape of the sensor elements.

10. The soil moisture sensor arrangement according to claim 8, wherein within the hollow space of the body of the housing includes a flowable and solidified material that envelops all of the at least two capacitive soil moisture sensor elements such that the capacitive soil moisture sensor elements have a fixed location relative to the housing.

11. The soil moisture sensor arrangement according to claim 8, wherein the body of the housing includes a flexible form into which two or more soil moisture sensor elements are located and further includes a material which is located inside the flexible form which stiffens the flexible form such that the body can be inserted into a prepared opening in the soil.

12. The soil moisture sensor arrangement according to claim 8, wherein each sensor element has a circular cross-sectional shape.

13. The soil moisture sensor arrangement according to claim 8, wherein for each capacitive soil moisture sensor, there are first and a second capacitive elements which are are spaced longitudinally along the housing, the first capacitive element being spaced from the second capacitive element and the second capacitive element being located closer to the inserted end than the first capacitive element.

14. The soil moisture sensor arrangement according to claim 2, wherein the external shape of the housing is in conformance with the outer shape of the sensor elements.

15. The soil moisture sensor arrangement according to claim 14, wherein the hollow space of the body of the housing includes material that envelops all of the at least two capacitive soil moisture sensor elements such that the capacitive soil moisture sensor elements have a fixed location relative to the housing.

16. The soil moisture sensor arrangement according to claim 14, wherein the body of the housing includes a flexible form into which two or more soil moisture sensor elements are located and further includes a material which is located inside the flexible form which stiffens the flexible form such that the body can be inserted into a prepared opening in the soil.

17. The soil moisture sensor arrangement according to claim 2, wherein within the hollow space of the body of the housing includes a flowable and solidified material that envelops all of the at least two capacitive soil moisture sensor elements such that the capacitive soil moisture sensor elements have a fixed location relative to the housing.

18. The soil moisture sensor arrangement according to claim 17, wherein the body of the housing includes a flexible form into which two or more soil moisture sensor elements are located and further includes a material which is located inside the flexible form which stiffens the flexible form such that the body can be inserted into a prepared opening in the soil.

19. The soil moisture sensor arrangement according to claim 2, wherein at least a portion of the body of the housing includes a flexible form into which the two or more capacitive soil moisture sensor elements are located and further includes a material which is located inside the flexible form which stiffens the flexible form such that the body can be inserted into a prepared opening in the soil.

20. The soil moisture sensor arrangement according to claim 2, wherein the body of the housing includes a flexible form into which two or more soil moisture sensor elements are located and further includes a material which is located inside the flexible form which stiffens the flexible form such that the body can be inserted into a prepared opening in the soil.

21. A method for installing a soil moisture sensor arrangement comprising a housing including an elongate body with a head end, an inserted end, and an outer surface being continuously tapered from the head end to the inserted end to form a hollow space therein, and at least one soil moisture sensor located within the housing, the method includes the steps of:
   a) preparing an opening in the soil having an inner wall converging to the region near the base of the opening; and
   b) inserting the housing into the prepared opening until the outer surface of the body of the housing is in contact with the soil sides of the prepared opening along the full length of the housing and each sensor provides for measurement of at least the moisture of the soil in which the sensor arrangement is inserted.

* * * * *